(12) United States Patent
Ueda et al.

(10) Patent No.: US 9,414,585 B2
(45) Date of Patent: Aug. 16, 2016

(54) CUPROUS OXIDE PARTICLE DISPERSION LIQUID, COATING AGENT COMPOSITION, AND ANTIBACTERIAL/ANTIVIRAL MEMBER

(71) Applicant: Panasonic Intellectual Property Management Co., Ltd., Osaka (JP)

(72) Inventors: Takeshi Ueda, Osaka (JP); Kensaku Kinugawa, Nara (JP); Daigo Yamashina, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 14/761,190

(22) PCT Filed: Feb. 24, 2014

(86) PCT No.: PCT/JP2014/000942
§ 371 (c)(1),
(2) Date: Jul. 15, 2015

(87) PCT Pub. No.: WO2014/132606
PCT Pub. Date: Sep. 4, 2014

(65) Prior Publication Data
US 2015/0351385 A1    Dec. 10, 2015

(30) Foreign Application Priority Data
Feb. 27, 2013   (JP) .................................. 2013-036790

(51) Int. Cl.
*A01N 25/04* (2006.01)
*A01N 59/20* (2006.01)
*A01N 25/30* (2006.01)
*B82Y 30/00* (2011.01)
*C09D 5/14* (2006.01)
*C09D 7/12* (2006.01)
*C09D 201/00* (2006.01)
*C09C 1/00* (2006.01)
*C08K 3/22* (2006.01)

(52) U.S. Cl.
CPC .............. *A01N 25/30* (2013.01); *A01N 25/04* (2013.01); *A01N 59/20* (2013.01); *C09C 1/00* (2013.01); *C09D 5/14* (2013.01); *C09D 7/12* (2013.01); *C09D 7/1266* (2013.01); *C09D 201/00* (2013.01); *B82Y 30/00* (2013.01); *C01P 2004/62* (2013.01); *C01P 2004/64* (2013.01); *C08K 3/22* (2013.01); *C08K 2003/2248* (2013.01)

(58) Field of Classification Search
None
See application file for complete search history.

(56) References Cited

U.S. PATENT DOCUMENTS

| 4,354,873 | A | * | 10/1982 | Supcoe | C09D 5/1675 106/18.32 |
| 7,354,596 | B1 | * | 4/2008 | Banovetz | A01N 25/10 424/405 |
| 7,674,401 | B2 | | 3/2010 | Maruyama | |
| 7,767,721 | B2 | | 8/2010 | Maruyama et al. | |
| 2005/0069648 | A1 | | 3/2005 | Maruyama | |
| 2006/0098065 | A1 | * | 5/2006 | Maruyama | C01G 3/02 347/100 |
| 2006/0099539 | A1 | * | 5/2006 | Ito | G03C 1/005 430/567 |
| 2015/0351385 | A1 | * | 12/2015 | Ueda | A01N 59/20 523/122 |

FOREIGN PATENT DOCUMENTS

| CN | 1606481 A | | 4/2005 |
| CN | 1720196 A | | 1/2006 |
| CN | 102211031 A | | 10/2011 |
| JP | 2004-277627 A | | 10/2004 |
| JP | 2004-323568 A | | 11/2004 |
| JP | 2005-015628 A | | 1/2005 |
| JP | 2008-282913 A | | 11/2008 |
| JP | 2010-239897 A | | 10/2010 |
| JP | 2011-001213 A | | 1/2011 |
| JP | 2011001213 A | * | 1/2011 |
| JP | 2012-129096 A | | 7/2012 |
| JP | 2012-134297 A | | 7/2012 |
| WO | WO 03/051562 A1 | | 6/2003 |
| WO | WO 2004/050559 A1 | | 6/2004 |

OTHER PUBLICATIONS

Chinese Office Action and Search Report with English translation dated Feb. 29, 2016 for corresponding Chinese Application No. 201480004748.7.
International Search Report for corresponding International Application No. PCT/JP2014/000942 mailed May 20, 2014.
Form PCT/ISA/237 for corresponding International Application No. PCT/JP2014/000942 dated May 20, 2014.

* cited by examiner

*Primary Examiner* — Peter A Salamon
(74) *Attorney, Agent, or Firm* — Renner, Otto, Boisselle & Sklar, LLP

(57) ABSTRACT

A cuprous oxide particle dispersion liquid includes: cuprous oxide particles; 20 to 100 parts by mass of a phosphate ester-based anionic surfactant per 100 parts by mass of the cuprous oxide particles; and 500 to 10000 parts by mass of an organic solvent per 100 parts by mass of the cuprous oxide particles. The cuprous oxide particles have an average primary particle diameter of 2 nm to 80 nm and have an average secondary particle diameter of 50 nm to 150 nm, the average secondary particle diameter being measured by dynamic light scattering using cumulant analysis. A coating agent composition includes the cuprous oxide particle dispersion liquid and a binder resin, wherein the cuprous oxide particles are contained in a range from 0.1 to 50 parts by mass in 100 parts by mass of a non-volatile matter content of the coating agent composition. An antibacterial/antiviral member includes a substrate and a coating film formed on the substrate and containing the coating agent composition.

3 Claims, No Drawings

CUPROUS OXIDE PARTICLE DISPERSION LIQUID, COATING AGENT COMPOSITION, AND ANTIBACTERIAL/ANTIVIRAL MEMBER

TECHNICAL FIELD

The present invention relates to a cuprous oxide particle dispersion liquid, a coating agent composition, and an antibacterial/antiviral member. More particularly, the present invention relates to a cuprous oxide particle dispersion liquid and a coating agent composition with high antibacterial and antiviral performances and transparency, and an antibacterial/antiviral member using the coating agent composition.

BACKGROUND ART

Various types of antibacterial members have been developed and turned into products to reduce microbes in the environment because of increased consumers' consciousness of hygiene. In general, antibacterial members used for interior members in houses or vehicles contain antibacterial materials such as silver and zinc. However, silver and zinc have a problem of costs or biological toxicity.

In view of such a problem, attempts to use cuprous oxide for antibacterial materials or virus inactivation agents are being developed, since an abundance of low-cost cuprous oxide with less biological toxicity is available (for example, refer to Patent Literature 1). However, the cuprous oxide is commonly used for concealing paint such as enamel for ship bottom painting because the cuprous oxide cannot be dispersed easily. In order to increase dispersibility, a method for producing a $Cu_2O$ nanoparticle dispersion liquid by way of microemulsion has been disclosed (for example, refer to Patent Literature 2).

CITATION LIST

Patent Literature

Patent Literature 1: Japanese Unexamined Patent Application Publication No. 2010-239897
Patent Literature 2: Japanese Unexamined Patent Application Publication No. 2011-001213

SUMMARY OF INVENTION

However, a bottom-up type synthesizing method such as a microemulsion method not only requires a complicated synthesizing process but also limits types of solvents used, which leads to a lot of problems of practical application.

The present invention has been made in view of the above-described conventional problems. An object of the present invention is to provide a cuprous oxide particle dispersion liquid and a coating agent composition capable of facilitating a synthesizing process and obtaining a coating film having sufficient transparency even when increasing a cuprous oxide concentration and improving an antibacterial property. Another object of the present invention is to provide an antibacterial/antiviral member using the coating agent composition.

A cuprous oxide particle dispersion liquid according to a first aspect of the present invention includes: cuprous oxide particles; 20 to 100 parts by mass of a phosphate ester-based anionic surfactant per 100 parts by mass of the cuprous oxide particles; and 500 to 10000 parts by mass of an organic solvent per 100 parts by mass of the cuprous oxide particles. The cuprous oxide particles have an average primary particle diameter of 2 nm to 80 nm and have an average secondary particle diameter of 50 nm to 150 nm, the average secondary particle diameter being measured by dynamic light scattering using cumulant analysis.

A coating agent composition according to a second aspect of the present invention includes the cuprous oxide particle dispersion liquid and a binder resin. The cuprous oxide particles are contained in a range from 0.1 to 50 parts by mass in 100 parts by mass of a non-volatile matter content of the coating agent composition.

An antibacterial/antiviral member according to a third aspect of the present invention includes a substrate and a coating film formed on the substrate and containing the coating agent composition.

DESCRIPTION OF EMBODIMENTS

Hereinafter, a cuprous oxide particle dispersion liquid, a coating agent composition, and an antibacterial/antiviral member according to the embodiment of the present invention will be explained in detail below.

[Cuprous Oxide Particle Dispersion Liquid]

The cuprous oxide particle dispersion liquid according to the present embodiment includes cuprous oxide particles, a phosphate ester-based anionic surfactant, and an organic solvent serving as a dispersion solvent for the cuprous oxide particles.

While a large amount of copper compounds exhibiting antibacterial activity have been reported, copper (I) oxide (cuprous oxide, $Cu_2O$) has higher antibacterial activity and antiviral activity than copper (II) oxide (CuO). Since copper ions tend to easily flow out of the cuprous oxide, the flowing copper ions come into contact with microbes or viruses and are thus coupled to enzymes or proteins so as to decrease the activity of the microbes or viruses and easily retard the metabolic function thereof. Further, the copper ions that flowed out convert oxygen in air into active oxygen due to the catalytic function of the copper ions so as to easily dissolve organic matter of the microbes or viruses. Therefore, the cuprous oxide particles to be used are preferably particles consisting of copper (I) oxide.

An average primary particle diameter of the cuprous oxide particles is in the range from 2 nm to 80 nm. When the average primary particle diameter of the cuprous oxide particles is smaller than 2 nm, the copper ions may not easily flow out because surface areas of the respective cuprous oxide particles are too small. When the average primary particle diameter of the cuprous oxide particles exceeds 80 nm, sufficiently ultrafine particles cannot be obtained by dispersion treatment described below. As a result, the cuprous oxide particles may be aggregated and precipitated during the dispersion treatment or during storage after the dispersion treatment. Here, the average primary particle diameter of the cuprous oxide particles can be obtained, for example, by measuring a plurality of diameters of the cuprous oxide particles with a transmission electron microscope (TEM).

The average primary particle diameter of the cuprous oxide particles is more preferably in the range from 10 nm to 70 nm, still more preferably in the range from 30 nm to 60 nm. The average primary particle diameter within the above-described range can finely disperse the cuprous oxide particles in the organic solvent while keeping the high surface areas of the cuprous oxide particles.

The cuprous oxide particle dispersion liquid according to the present embodiment includes the phosphate ester-based anionic surfactant in order to improve dispersion performance of the cuprous oxide particles in the organic solvent. The use of the phosphate ester-based anionic surfactant can increase the dispersion performance while suppressing a decrease of the antibacterial activity and the antiviral activity of the cuprous oxide particles. Examples of the phosphate ester-based anionic surfactant include alkyl phosphate salts, polyoxyethylene alkyl ether phosphate salts, and polyoxyethylene alkyl phenyl ether phosphate salts. More specific examples thereof include alkyl phosphate ester, polyoxyethylene alkyl ether phosphate ester, and polyoxyethylene (mono- or di-)alkyl phenyl ether phosphate ester. Other examples include phosphate ester of a polyoxyethylene (mono-, di- or tri-)alkyl phenyl ether polymer, and polyoxyethylene (mono-, di- or tri-)phenyl phenyl ether phosphate ester. Still other examples include polyoxyethylene (mono-, di- or tri-)benzyl phenyl ether phosphate ester, and polyoxyethylene (mono-, di- or tri-)styryl phenyl ether phosphate ester. Still other examples include phosphate ester of a polyoxyethylene (mono-, di- or tri-)styryl phenyl ether polymer, and phosphate ester of a polyoxyethylene polyoxypropylene block polymer. In addition, phosphate ester such as phosphatidylcholine, phosphatidyl ethanolimine, and condensed phosphoric acid (such as tripolyphosphate) may be used. Further, salts of the phosphate ester described above may also be used. Each of these materials used as the phosphate ester-based anionic surfactant may be used independently, or two or more kinds thereof may be combined together.

Although the organic solvent serving as a dispersion medium for the cuprous oxide particles is not particularly limited, a solvent capable of easily volatilizing when being applied and suppressing hardening inhibition at the time of forming a coating film, is preferably selected as appropriate. Examples of the organic solvent include aromatic hydrocarbons (such as toluene and xylene), alcohols (such as methanol, ethanol, and isopropyl alcohol), and ketones (such as acetone, methyl ethyl ketone, and methyl isobutyl ketone). Other examples include aliphatic hydrocarbons (such as hexane and heptane), ethers (such as tetrahydrofuran), and amide solutions (such as N,N-dimethylformamide (DMF) and dimethylacetamide (DMAc)). Among these, the aromatic hydrocarbons and the alcohols are particularly preferable. Each of these materials used as the organic solvent may be used independently, or two or more kinds thereof may be combined together.

The added amount of the phosphate ester-based anionic surfactant in the cuprous oxide particle dispersion liquid can be adjusted as appropriate depending on the content of the cuprous oxide particles. In particular, the content of the phosphate ester-based anionic surfactant is in the range from 20 to 100 parts by mass with respect to 100 parts by mass of the cuprous oxide particles. When the content of the phosphate ester-based anionic surfactant is less than 20 parts by mass, sufficient dispersibility may not be ensured because the cuprous oxide particles are aggregated with each other. When the content of the phosphate ester-based anionic surfactant exceeds 100 parts by mass, hardening inhibition may be caused when the surfactant is mixed with binder resin to form a coating film as described below. In addition, the content exceeding 100 parts by mass may also decrease physical properties of the coating film such as film formation performance and adhesion performance.

The added amount of the phosphate ester-based anionic surfactant is more preferably in the range from 20 to 90 parts by mass, particularly preferably in the range from 30 to 70 parts by mass, with respect to 100 parts by mass of the cuprous oxide particles. The added amount within the range described above can improve the dispersibility of the cuprous oxide particles and prevent a decrease of the physical properties of the coating film.

The added amount of the organic solvent in the cuprous oxide particle dispersion liquid can also be adjusted as appropriate depending on the content of the cuprous oxide particles. In particular, the content of the organic solvent is in the range from 500 to 10000 parts by mass with respect to 100 parts by mass of the cuprous oxide particles. When the content of the organic solvent is less than 500 parts by mass, the dispersibility of the cuprous oxide particles may decrease, and the efficiency of the application operation may decrease because viscosity of the cuprous oxide particle dispersion liquid increases. When the content of the organic solvent exceeds 10000 parts by mass, the operation efficiency may decrease because the coating film formation performance (drying performance) of the coating film formed when being mixed with the binder resin decreases.

The added amount of the organic solvent is more preferably in the range from 1000 to 5000 parts by mass with respect to 100 parts by mass of the cuprous oxide particles. The added amount within such a range can improve the dispersibility of the cuprous oxide particles and prevent an excessive increase in viscosity.

As described below, the cuprous oxide particle dispersion liquid forms a coating agent composition when being mixed with the binder resin, and the coating agent composition forms an antibacterial/antiviral coating film when being applied to a substrate. In order to improve transparency of the coating film, an average secondary particle diameter of the cuprous oxide particles in the cuprous oxide particle dispersion liquid is required to be in the range from 50 nm to 150 nm. When the average secondary particle diameter is less than 50 nm, the primary particles in which a crystal structure is destroyed due to excessive dispersion treatment coexist with the dispersed secondary particles, which may cause a decrease of photocatalytic activity. When the average secondary particle diameter exceeds 150 nm, the antibacterial performance may decrease because the surface areas of the cuprous oxide particles decrease. Note that, in the present description, the average secondary particle diameter used is measured by a dynamic light scattering method and obtained by cumulant analysis.

The content of the cuprous oxide particles is preferably greater than or equal to 1 part by mass, more preferably greater than or equal to 8 parts by mass, in 100 parts by mass of a non-volatile matter content of the cuprous oxide particle dispersion liquid according to the present embodiment. The effects according to the present embodiment may be obtained even when the content of the cuprous oxide particles is less than 1 part by mass in 100 parts by mass of the total non-volatile matter content. However, when such cuprous oxide particle dispersion liquid is mixed with the binder resin, the solvent component of the coating agent composition is excessively large. This may cause liquid leakage of the coating agent composition at the time of application to result in impaired appearance, and may further cause a decrease of the physical properties because of insufficiency of the coating film thickness. The upper limit of content of the cuprous oxide particles in the cuprous oxide particle dispersion liquid is not particularly limited as long as sufficient transparency of the coating film to be obtained is ensured. For example, the content of the cuprous oxide particles may be less than or equal to 50 parts by mass in 100 parts by mass of the non-volatile matter content of the cuprous oxide particle dispersion liquid. Here, the non-volatile matter content in the present description may be measured in accordance with Japanese Industrial Standards JIS K5601-1-2 (Testing methods for paint components-Part 1: General rule-Section 2: Determination of non-volatile matter content).

As described above, the cuprous oxide particle dispersion liquid according to the present embodiment includes the cuprous oxide particles, the phosphate ester-based anionic surfactant, and the organic solvent. The content of the phosphate ester-based anionic surfactant is in the range from 20 to 100 parts by mass, and the content of the organic solvent is in the range from 500 to 10000 parts by mass, with respect to 100 parts by mass of the cuprous oxide particles. The cuprous oxide particles in the cuprous oxide particle dispersion liquid have the average primary particle diameter in the range from 2 nm to 80 nm and the average secondary particle diameter, which is measured by the dynamic light scattering method and obtained by the cumulant analysis, in the range from 50 nm to 150 nm. The cuprous oxide particle dispersion liquid having such a constitution can improve the dispersibility of the cuprous oxide particles even when the concentration of the cuprous oxide particles in the cuprous oxide particle dispersion liquid increases, so as to ensure sufficient transparency of the antibacterial/antiviral film using the cuprous oxide particle dispersion liquid.

[Method for Manufacturing Cuprous Oxide Particle Dispersion Liquid]

Next, a method for manufacturing the cuprous oxide particle dispersion liquid described above is explained below. The cuprous oxide particle dispersion liquid can be prepared in a manner such that the cuprous oxide particles, the phosphate ester-based anionic surfactant and the organic solvent are mixed together, and the cuprous oxide particles are finely dispersed in the organic solvent. Therefore, any methods may be used as long as the cuprous oxide particles can be finely dispersed.

However, in order to improve the dispersibility of the cuprous oxide particles and easily ensure the transparency of the antibacterial/antiviral film, the process of dispersing the cuprous oxide particles is preferably divided into pre-dispersion treatment and main dispersion treatment. The pre-dispersion treatment can wet surfaces of the cuprous oxide particles and replace air layers on the surfaces with the organic solvent so that the dispersion immediately proceeds in the following main dispersion treatment. If the pre-dispersion treatment is insufficient, the dispersion proceeds slowly, which may apply unnecessary mechanical impact to the cuprous oxide particles. As a result, the crystal structure of the cuprous oxide particles itself is destroyed, which may lead to a dispersion liquid with decreased stability.

The stirring step in the pre-dispersion treatment may be carried out by use of a common dissolver. However, in order to easily wet the surfaces of the cuprous oxide particles, the stirring step is preferably carried out by use of a high-speed stirrer. For example, T. K. Homomixer, T. K. Robomix, or T. K. Filmix (trade names, manufactured by PRIMIX Corporation) may be used as the high-speed stirrer. Alternatively, CLEAMIX (registered trademark) (trade name, manufactured by M Technique Co., Ltd.) or Ultradisper (trade name, manufactured by Asada Iron Works Co., Ltd.) may also be used.

A dispersing apparatus used in the main dispersion treatment may be a kneading machine such as a kneader, a two-roll mill, a three-roll mill, SS5 (trade name, manufactured by M Technique Co., Ltd.), and MIRACLE KCK (registered trademark) (trade name, manufactured by Asada Iron Works Co., Ltd.). Other examples of the dispersing apparatus include a ultrasonic dispersing machine, Microfluidizer (trade name, manufactured by Mizuho Industrial Co., Ltd.) as a high-pressure homogenizer, and NanoVater (registered trademark) (trade name, manufactured by Yoshida Kikai Co., Ltd.). Further, Starburst (registered trademark) (trade name, manufactured by Sugino Machine Ltd.) or G-smasher (trade name, Rix Corporation) may also be used. When bead media such as glass or zircon are used, a ball mill, a bead mill, a sand mill, a horizontal media mill dispersing apparatus, or a colloid mill may be used. Bead media used in a bead mill preferably have a diameter of 1 mm or smaller, more preferably have a diameter of 0.5 mm or smaller. Here, the dispersion time in the pre-dispersion treatment and the main dispersion treatment may be adjusted as appropriate depending on the type of the dispersing apparatus and media so that the cuprous oxide particles are finely dispersed in the organic solvent together with the phosphate ester-based anionic surfactant.

In the process of supplying the processed liquid subjected to the pre-dispersion treatment to the aforementioned dispersing apparatus, the processed liquid may be simultaneously stirred sufficiently with a high-speed stirrer or the like. This can shorten the process time.

[Coating Agent Composition]

The coating agent composition according to the present embodiment includes the cuprous oxide particle dispersion liquid described above and the binder resin. As described above, since the cuprous oxide particle dispersion liquid has an increased cuprous oxide concentration and improved dispersibility, the coating agent composition using such cuprous oxide particle dispersion liquid can form a coating film having a high antibacterial/antiviral property and high transparency.

The binder resin mixed together with the cuprous oxide particle dispersion liquid is not particularly limited as long as the coating film formed of the coating agent composition can ensure sufficient stability, antibacterial/antiviral property and transparency. Examples of the binder resin include alkyd resin, acrylic resin, melamine resin, urethane resin, epoxy resin, and silicone resin. In addition, polyester resin, polyamic acid resin, polyimide resin, styrene-maleic acid resin, or styrene-maleic anhydride resin may also be used. Further, various types of acrylic monomers or acrylate monomers may be applicable. Particularly preferable examples of resin or a monomer as the binder resin include urethane resin, acrylic resin, acrylic monomers, polyamic acid resin, polyimide resin, styrene-maleic acid resin, and styrene-maleic anhydride resin. Each of these materials used as the binder resin may be used independently, or two or more kinds thereof may be combined together.

The coating agent composition may further include various types of additives to be combined together, in addition to the cuprous oxide particle dispersion liquid and the binder resin, as long as the additives do not influence the antibacterial activity. In particular, a dispersant, a pigment, a filler, an aggregate, a thickener, a flow control agent, a leveling agent, a curing agent, a cross-linker, or a curing catalyst may be combined together.

The coating agent composition according to the present embodiment can be prepared in a manner such that the cuprous oxide particle dispersion liquid and the binder resin, and the additive described above as necessary are mixed together. The mixing process may be carried out by use of, for example, the dissolver or the high-speed stirrer described above.

The cuprous oxide particles are preferably contained in the range from 0.1 to 50 parts by mass in 100 parts by mass of the non-volatile matter content of the coating agent composition. When the content of the cuprous oxide particles in the non-volatile matter content is less than 0.1 part by mass, the antibacterial performance may be deteriorated since the content of the cuprous oxide particles is insufficient. When the content of the cuprous oxide particles exceeds 50 parts by mass, the antibacterial performance may be ensured sufficiently, but the physical properties of the coating film may decrease since the content of the binder resin is insufficient.

The content of the cuprous oxide particles is more preferably in the range from 0.1 to 10 parts by mass in 100 parts by mass of the non-volatile matter content of the coating agent composition. The content of the cuprous oxide particles within such a range can prevent a decrease of the physical properties of the coating film and ensure high transparency while exhibiting sufficient antibacterial/antiviral performance.

[Antibacterial/Antiviral Member]

The antibacterial/antiviral member according to the present embodiment includes: a substrate; and a coating film formed on the substrate and containing the coating agent composition. As described above, the coating agent composition according to the present embodiment has a high antibacterial/antiviral property derived from the cuprous oxide particles. Further, since the cuprous oxide particles are finely dispersed in the coating agent composition, the coating film formed thereof has high transparency.

In the present embodiment, the substrate may basically include any material such as an organic polymer, ceramics, metal, glass, plastic, decorative plywood, or composites of these materials. The shape of the substrate is not particularly limited and may be a simple or complicated shape such as a plate shape, a spherical shape, a round column, a cylindrical shape, a rod shape, a prism, or a hollow prism. Alternatively, the substrate may be a porous body such as a filter.

The substrate is preferably used for construction materials such as ceiling materials, tiles, glass, wallpaper, wall materials, floors, or fixture materials, interior materials for vehicles (instrument panels, seats, or ceilings), electrical appliances such as refrigerators or air conditioners, textile products such as clothing or curtains, industrial equipment, or medical equipment. The substrate is also preferably used for doors, door handles, pulls, railings, interior counters, furniture, kitchens, toilets, bath rooms, lighting fixtures, touch panels, switches, or sheets used therein. The coating film including the coating agent composition according to the present embodiment is particularly effectively used for surfaces on which human bodies or the like frequently touch due to the high antibacterial/antiviral property of the coating film.

The antibacterial/antiviral material according to the present embodiment may be applied to filters for air purifiers or for air conditioners. The antibacterial/antiviral material is effective when used not only in houses but also in other places where large numbers of people use such as hospitals and homes for elderly people, and public transportation such as trains, buses, and planes, since the use of the antibacterial/antiviral material can reduce the risk of a bacterial or viral infection.

The antibacterial/antiviral member according to the present embodiment can be obtained in a manner such that the coating agent composition is applied to the substrate and is then dried. The applying method and the drying method in this case are not particularly limited. Examples of the method of applying the coating agent composition to at least part of the substrate include screen printing, spin coating, dip coating, roll coating, brush coating, spray coating, and ink jet coating. The drying conditions are not particularly limited as long as the organic solvent can be removed.

The thickness of the coating film applied with the coating agent composition after hardening is preferably in the range from 2 μm to 15 μm, more preferably in the range from 4 μm to 13 μm. The thickness after the hardening within the range described above can improve surface hardness of the hardened film and increase adhesion performance.

As described above, the antibacterial/antiviral member according to the present embodiment includes the substrate and the coating film formed on the substrate and containing the coating agent composition. The nano-size cuprous oxide particles are dispersed in the coating agent composition with high concentration. Therefore, the antibacterial/antiviral member can ensure both high antibacterial/antiviral performance derived from the cuprous oxide particles and sufficient transparency.

EXAMPLES

The following are further specific explanations of the present invention with reference to examples and comparative examples; however, the present invention is not limited to these examples.

Example 1

First, cuprous oxide (manufactured by Sigma-Aldrich Corporation) (average primary particle diameter: 50 nm, CuO reduction) was prepared as cuprous oxide particles, and methyl ethyl ketone (MEK) was prepared as an organic solvent. Further, DISPARLON (registered trademark) PW-36 (manufactured by Kusumoto Chemicals, Ltd.) was prepared as a phosphate ester-based anionic surfactant.

Next, 100 parts by mass of the cuprous oxide, 1000 parts by mass of the methyl ethyl ketone, and 30 parts by mass of the phosphate ester-based anionic surfactant were mixed together, and then stirred, as pre-dispersion treatment, by use of a stirrer (T. K. Robomix, manufactured by PRIMIX Corporation) at 8000 rpm for 30 minutes.

Subsequently, 1 L of the processed liquid obtained by the pre-dispersion treatment was stirred by use of the stirrer (T. K. Robomix, manufactured by PRIMIX Corporation) at 3000 rpm, and then subjected to main dispersion treatment by use of a dispersing apparatus (PICOMILL, manufactured by Asada Iron Works Co., Ltd.). Here, zirconia beads with a size of 0.3 mm were used as dispersion media in the dispersing apparatus and circulated for two hours to carry out the dispersion treatment. As a result, a cuprous oxide particle dispersion liquid according to this example in which a cuprous oxide concentration was 9% by mass was prepared. Further, 23 parts by mass of the cuprous oxide particle dispersion liquid thus obtained and 10 parts by mass of the binder resin were mixed together so as to prepare a coating agent composition according to this example. The binder resin used was obtained as follows.

First, ACRYDIC (registered trademark) A-801 (manufactured by DIC Corporation) as isocyanate curing acrylic resin and DURANATE (registered trademark) TPA100 (manufactured by Asahi Kasei Chemicals Corporation) were mixed together in a manner such that an isocyanate group and a hydroxyl group fulfilled the condition of NCO/OH=1. Next, the mixture thus obtained was diluted by use of methyl ethyl ketone in a manner such that a non-volatile matter content was 20% by mass so as to prepare the binder resin.

Example 2

A cuprous oxide particle dispersion liquid of this example was prepared by the same process as in Example 1 except that 100 parts by mass of the cuprous oxide, 1000 parts by mass of the methyl ethyl ketone, and 20 parts by mass of the phosphate ester-based anionic surfactant were mixed together. The cuprous oxide concentration in the cuprous oxide particle dispersion liquid of this example was 9% by mass.

Subsequently, 22 parts by mass of the cuprous oxide particle dispersion liquid thus obtained and 10 parts by mass of the binder resin were mixed together in the same manner as in Example 1 so as to prepare a coating agent composition according to this example.

Example 3

A cuprous oxide particle dispersion liquid of this example was prepared by the same process as in Example 1 except that 100 parts by mass of the cuprous oxide, 1000 parts by mass of the methyl ethyl ketone, and 90 parts by mass of the phosphate ester-based anionic surfactant were mixed together. The cuprous oxide concentration in the cuprous oxide particle dispersion liquid of this example was 8% by mass.

Subsequently, 24 parts by mass of the cuprous oxide particle dispersion liquid thus obtained and 10 parts by mass of the binder resin were mixed together in the same manner as in Example 1 so as to prepare a coating agent composition according to this example.

Example 4

A cuprous oxide particle dispersion liquid of this example was prepared by the same process as in Example 1 except that 100 parts by mass of the cuprous oxide, 500 parts by mass of the methyl ethyl ketone, and 30 parts by mass of the phosphate ester-based anionic surfactant were mixed together. The cuprous oxide concentration in the cuprous oxide particle dispersion liquid of this example was 16% by mass.

Subsequently, 13 parts by mass of the cuprous oxide particle dispersion liquid thus obtained and 10 parts by mass of the binder resin were mixed together in the same manner as in Example 1 so as to prepare a coating agent composition according to this example.

Example 5

First, cuprous oxide (manufactured by Sigma-Aldrich Corporation) (average primary particle diameter: 50 nm, CuO reduction) was prepared as cuprous oxide particles, and diethylene glycol monomethyl ether (DEGME) was prepared as an organic solvent. Further, DISPARLON (registered trademark) PW-36 (manufactured by Kusumoto Chemicals, Ltd.) was prepared as a phosphate ester-based anionic surfactant.

Next, 100 parts by mass of the cuprous oxide, 10000 parts by mass of the diethylene glycol monomethyl ether, and 30 parts by mass of the phosphate ester-based anionic surfactant were mixed together, and then subjected to pre-dispersion treatment and main dispersion treatment in the same manner as in Example 1. Thus, a cuprous oxide particle dispersion liquid according to this example in which a cuprous oxide concentration was 1% by mass was prepared.

Subsequently, 203 parts by mass of the cuprous oxide particle dispersion liquid thus obtained and 10 parts by mass of binder resin were mixed together so as to prepare a coating agent composition according to this example. Here, the binder resin used in this example was the same as that in Example 1.

Example 6

A cuprous oxide particle dispersion liquid of this example was prepared by the same process as in Example 5 except that 100 parts by mass of the cuprous oxide, 500 parts by mass of the diethylene glycol monomethyl ether, and 30 parts by mass of the phosphate ester-based anionic surfactant were mixed together. The cuprous oxide concentration in the cuprous oxide particle dispersion liquid of this example was 16% by mass.

Subsequently, 0.1 part by mass of the cuprous oxide particle dispersion liquid thus obtained and 10 parts by mass of the binder resin were mixed together in the same manner as in Example 5 so as to prepare a coating agent composition according to this example.

Example 7

A cuprous oxide particle dispersion liquid of this example was prepared by the same process as in Example 5 except that 100 parts by mass of the cuprous oxide, 500 parts by mass of the diethylene glycol monomethyl ether, and 30 parts by mass of the phosphate ester-based anionic surfactant were mixed together. The cuprous oxide concentration in the cuprous oxide particle dispersion liquid of this example was 16% by mass.

Subsequently, 29 parts by mass of the cuprous oxide particle dispersion liquid thus obtained and 10 parts by mass of the binder resin were mixed together in the same manner as in Example 5 so as to prepare a coating agent composition according to this example.

Comparative Example 1

First, cuprous oxide (manufactured by Sigma-Aldrich Corporation) (average primary particle diameter: 50 nm, CuO reduction) was prepared as cuprous oxide particles, and methyl ethyl ketone (MEK) was prepared as an organic solvent.

Next, 100 parts by mass of the cuprous oxide and 1000 parts by mass of the methyl ethyl ketone were mixed together, and then stirred, as pre-dispersion treatment, by use of a stirrer (T. K. Robomix, manufactured by PRIMIX Corporation) at 8000 rpm for 30 minutes.

Subsequently, 1 L of the processed liquid obtained by the pre-dispersion treatment was stirred by use of the stirrer (T. K. Robomix, manufactured by PRIMIX Corporation) at 3000 rpm, and then supposed to be subjected to main dispersion treatment by use of a dispersing apparatus (PICOMILL, manufactured by Asada Iron Works Co., Ltd.). However, the main dispersion treatment could not be conducted because the viscosity of the processed liquid obtained by the pre-dispersion treatment did not decrease to a level sufficient to supply the processed liquid to the dispersing apparatus.

Comparative Example 2

A cuprous oxide particle dispersion liquid of this comparative example was supposed to be prepared by the same process as in Example 1 except that 100 parts by mass of the cuprous oxide, 1000 parts by mass of the methyl ethyl ketone, and 10 parts by mass of the phosphate ester-based anionic surfactant were mixed together. However, the main dispersion treatment could not be conducted because the viscosity of the processed liquid obtained by the pre-dispersion treatment did not decrease to a level sufficient to supply the processed liquid to the dispersing apparatus, as in the case of Comparative Example 1.

Comparative Example 3

A cuprous oxide particle dispersion liquid of this comparative example was prepared by the same process as in Example 1 except that 100 parts by mass of the cuprous oxide, 1000 parts by mass of the methyl ethyl ketone, and 150 parts by mass of the phosphate ester-based anionic surfactant were mixed together. The cuprous oxide concentration in the cuprous oxide particle dispersion liquid of this comparative example was 8% by mass.

Subsequently, 25 parts by mass of the cuprous oxide particle dispersion liquid thus obtained and 10 parts by mass of the binder resin were mixed together in the same manner as in Example 1 so as to prepare a coating agent composition according to this comparative example.

Comparative Example 4

A cuprous oxide particle dispersion liquid of this comparative example was supposed to be prepared by the same process as in Example 1 except that 100 parts by mass of the cuprous oxide, 300 parts by mass of the methyl ethyl ketone, and 30 parts by mass of the phosphate ester-based anionic surfactant were mixed together. However, the main dispersion treatment could not be conducted because the viscosity of the processed liquid obtained by the pre-dispersion treatment did not decrease to a level sufficient to supply the processed liquid to the dispersing apparatus, as in the case of Comparative Example 1.

Comparative Example 5

A cuprous oxide particle dispersion liquid of this comparative example was prepared by the same process as in Example 1 except that 100 parts by mass of the cuprous oxide, 15000 parts by mass of the methyl ethyl ketone, and 10 parts by mass of the phosphate ester-based anionic surfactant were mixed together. The cuprous oxide concentration in the cuprous oxide particle dispersion liquid of this comparative example was 0.7% by mass.

Subsequently, 22 parts by mass of the cuprous oxide particle dispersion liquid thus obtained and 10 parts by mass of the binder resin were mixed together in the same manner as in Example 1 so as to prepare a coating agent composition according to this comparative example.

Comparative Example 6

A cuprous oxide particle dispersion liquid of this comparative example was prepared by the same process as in Example 1 except that DISPERBYK (registered trademark) (manufactured by BYK-Chemie Japan K. K.) 111 was used as a surfactant. The cuprous oxide concentration in the cuprous oxide particle dispersion liquid of this comparative example was 9% by mass.

Subsequently, 23 parts by mass of the cuprous oxide particle dispersion liquid thus obtained and 10 parts by mass of the binder resin were mixed together in the same manner as in Example 1 so as to prepare a coating agent composition according to this comparative example.

Comparative Example 7

First, cuprous oxide (manufactured by Sigma-Aldrich Corporation) (average primary particle diameter: 500 nm, CuO reduction) was prepared as cuprous oxide particles, and methyl ethyl ketone was prepared as an organic solvent. Further, DISPARLON (registered trademark) PW-36 (manufactured by Kusumoto Chemicals, Ltd.) was prepared as a phosphate ester-based anionic surfactant.

Next, 100 parts by mass of the cuprous oxide, 1000 parts by mass of the methyl ethyl ketone, and 10 parts by mass of the phosphate ester-based anionic surfactant were mixed together, and then subjected to pre-dispersion treatment and main dispersion treatment in the same manner as in Example 1. Thus, a cuprous oxide particle dispersion liquid according to this comparative example in which a cuprous oxide concentration was 9% by mass was prepared.

Subsequently, 23 parts by mass of the cuprous oxide particle dispersion liquid thus obtained and 10 parts by mass of binder resin were mixed together so as to prepare a coating agent composition according to this comparative example. Here, the binder resin used in this comparative example was the same as that in Example 1.

Comparative Example 8

A coating agent composition according to this comparative example was prepared in a manner such that 128 parts by mass of the cuprous oxide particle dispersion liquid obtained in Example 1 and 10 parts by mass of binder resin were mixed together. The binder resin used in this comparative example was the compound used in Example 1.

Comparative Example 9

A coating agent composition according to this comparative example was prepared in a manner such that 1 part by mass of the cuprous oxide particle dispersion liquid obtained in Example 1 and 10 parts by mass of binder resin were mixed together. The binder resin used in this comparative example was the compound used in Example 1.

Tables 1 and 2 show the added amount and the average primary particle diameter of the cuprous oxide particles, the added amount of the organic solvent, the added amount of the surfactant, the concentration of the cuprous oxide particles in the cuprous oxide particle dispersion liquid, and the mixed amounts of the cuprous oxide particle dispersion liquid and the binder resin in the coating agent composition in each of examples and comparative examples.

stirrer could be transferred to the dispersing apparatus from the stirrer via a fluid transfer pump so as to be subjected to the main dispersion treatment by use of the dispersing apparatus. The examples in which the processed liquid could be transferred to the dispersing apparatus are indicated by "○", and the examples in which the processed liquid could not be transferred to the dispersing apparatus because of excessively high viscosity of the processed liquid are indicated by "x". Here, the fluid transfer pump used was a Masterflex fluid transfer pump (manufactured by Masterflex) including a PTFE pump head.

TABLE 1

| | Cuprous Oxide | | Organic Solvent Added Amount | | Surfactant Added | Cuprous Oxide Particle Concentration in Dispersion Liquid (% by Mass) | Mixed Amount of Cuprous Oxide Particle Dispersion Liquid (Parts by Mass) | Mixed Amount of Binder Resin (Parts by Mass) |
| | Added Amount (Parts by Mass) | Average Primary Particle Diameter (nm) | MEK (Parts by Mass) | DEGME (Parts by Mass) | Amount (Parts by Mass) | | | |
|---|---|---|---|---|---|---|---|---|
| Example 1 | 100 | 50 | 1000 | — | 30 | 9 | 23 | 10 |
| Example 2 | 100 | 50 | 1000 | — | 20 | 9 | 22 | 10 |
| Example 3 | 100 | 50 | 1000 | — | 90 | 8 | 24 | 10 |
| Example 4 | 100 | 50 | 500 | — | 30 | 16 | 13 | 10 |
| Example 5 | 100 | 50 | — | 10000 | 30 | 1 | 203 | 10 |
| Example 6 | 100 | 50 | — | 500 | 30 | 16 | 0.1 | 10 |
| Example 7 | 100 | 50 | — | 500 | 30 | 16 | 29 | 10 |

TABLE 2

| | Cuprous Oxide | | Organic Solvent Added Amount | | Surfactant Added | Cuprous Oxide Particle Concentration in Dispersion Liquid (% by Mass) | Mixed Amount of Cuprous Oxide Particle Dispersion Liquid (Parts by Mass) | Mixed Amount of Binder Resin (Parts by Mass) |
| | Added Amount (Parts by Mass) | Average Primary Particle Diameter (nm) | MEK (Parts by Mass) | DEGME (Parts by Mass) | Amount (Parts by Mass) | | | |
|---|---|---|---|---|---|---|---|---|
| Comparative Example 1 | 100 | 50 | 1000 | — | 0 | — | — | — |
| Comparative Example 2 | 100 | 50 | 1000 | — | 10 | — | — | — |
| Comparative Example 3 | 100 | 50 | 1000 | — | 150 | 8 | 25 | 10 |
| Comparative Example 4 | 100 | 50 | 300 | — | 30 | — | — | — |
| Comparative Example 5 | 100 | 50 | 15000 | — | 10 | 0.7 | 22 | 10 |
| Comparative Example 6 | 100 | 50 | 1000 | — | 30 | 9 | 23 | 10 |
| Comparative Example 7 | 100 | 500 | 1000 | — | 10 | 9 | 23 | 10 |
| Comparative Example 8 | 100 | 50 | 1000 | — | 30 | 9 | 128 | 10 |
| Comparative Example 9 | 100 | 50 | 1000 | — | 30 | 9 | 1 | 10 |

The following evaluation tests were performed on the cuprous oxide particle dispersion liquid and the coating agent composition obtained in each of examples and comparative examples. Tables 3 and 4 show the results of the evaluation tests.

[Dispersion Property]

Evaluation was conducted to determine whether the processed liquid after the pre-dispersion treatment by use of the

[Measurement of Average Secondary Particle Diameter]

The cuprous oxide particle dispersion liquid obtained in each example was observed by a dynamic light scattering method and subjected to cumulant analysis so as to measure the average secondary particle diameter of the cuprous oxide particles. The particle diameter was measured by use of a concentrated system particle size analyzer FPAR-1000 (manufactured by Otsuka Electronics Co., Ltd.).

[Stability]

The cuprous oxide particle dispersion liquid obtained in each example was filled in a sample bottle with a volume of 50 cc and left for a week at a room temperature (25° C.). The bottom surface of the sample bottle was then visually observed to determine whether any precipitates were confirmed. The examples in which no precipitate was visually recognized are indicated by "o", and the examples in which some precipitates were visually recognized are indicated by "x".

[Transparency]

The cuprous oxide particle dispersion liquid obtained in each example was adjusted to have a cuprous oxide concentration of 1% by mass by use of methyl ethyl ketone. Subsequently, the diluted cuprous oxide particle dispersion liquid was applied to a glass plate by use of a bar coater #10. Thereafter, the coating film thus obtained was dried at 50° C. for 30 minutes. The haze value of the coating film after dried was evaluated by use of a haze meter NDH 4000 (manufactured by Nippon Denshoku Industries Co., Ltd.). The examples in which the haze value was 3 or below are indicated by "o", and the examples in which the haze value was 3 or higher are indicated by "x".

[Antibacterial Performance]

Evaluation of the antibacterial performance was conducted in accordance with JIS Z2801 (Antibacterial products-Tests for antibacterial activity and efficacy) by use of *Escherichia coli*. The examples in which the value of the antibacterial activity per hour was 3 or greater are indicated by "o", and the examples in which the value of the antibacterial activity was below 3 are indicated by "x".

[Film Formation Performance]

The coating agent composition obtained in each of examples and comparative examples was applied on a glass plate having a thickness of 2 mm and a size of 10 cm×10 cm by use of a bar coater #10. Subsequently, the applied coating agent composition was dried at 100° C. for 30 seconds to prepare a coating film for each example.

Thereafter, the coating film obtained in each example was touched with a finger to evaluate a dried condition thereof. In particular, the middle of the coating film in each example was touched with a finger. The examples in which no fingerprint could be visually recognized are indicated by "o", and the examples in which a fingerprint was visually recognized are indicated by "x".

[Adhesion Performance (Sticking Performance)]

Evaluation of adhesion performance was conducted on the coating film obtained in the evaluation of the film formation performance in each of examples and comparative examples at a cut interval of 1 mm in accordance with a cross-cut method prescribed in JIS K5600 (Testing methods for paints). The examples in which no abrasion was confirmed are indicated by "o", the examples in which some abrasion was confirmed are indicated by "x".

TABLE 3

| | Dispersion Property | Average Secondary Particle Diameter (nm) | Transparency | Stability | Antibacterial Performance | Film Formation Performance | Adhesion Performance |
|---|---|---|---|---|---|---|---|
| Example 1 | o | 82 | o | o | o | o | o |
| Example 2 | o | 93 | o | o | o | o | o |
| Example 3 | o | 85 | o | o | o | o | o |
| Example 4 | o | 90 | o | o | o | o | o |
| Example 5 | o | 85 | o | o | o | o | o |
| Example 6 | o | 82 | o | o | o | o | o |
| Example 7 | o | 82 | o | o | o | o | o |

TABLE 4

| | Dispersion Property | Average Secondary Particle Diameter (nm) | Transparency | Stability | Antibacterial Performance | Film Formation Performance | Adhesion Performance |
|---|---|---|---|---|---|---|---|
| Comparative Example 1 | x | — | — | — | — | — | — |
| Comparative Example 2 | x | — | — | — | — | — | — |
| Comparative Example 3 | o | 94 | o | o | o | x | x |
| Comparative Example 4 | x | — | — | — | — | — | — |
| Comparative Example 5 | o | 80 | o | o | x | o | o |
| Comparative Example 6 | o | 120 | o | o | x | o | o |
| Comparative Example 7 | o | 800 | x | o | x | o | o |
| Comparative Example 8 | o | 82 | o | o | o | o | x |
| Comparative Example 9 | o | 82 | o | o | x | o | o |

As shown in Table 3, the cuprous oxide particle dispersion liquid in each of Examples 1 to 7 exhibited a good result in the evaluation of dispersion property, and the obtained coating agent composition also exhibited good results in the evaluations of transparency, stability, antibacterial performance, film formation performance, and adhesion performance.

On the other hand, in Comparative Example 1 not containing the surfactant, Comparative Example 2 in which the added amount of the surfactant was small, and Comparative Example 4 in which the added amount of the organic solvent was small, the cuprous oxide particle dispersion liquid could not be prepared because the viscosity of the dispersion liquid increased. In Comparative Example 3 excessively containing the surfactant, the physical properties of the coating film such as film formation performance and adhesion performance decreased. In Comparative Example 5 excessively containing the organic solvent, the antibacterial performance decreased. In the case where the surfactant was not the phosphate ester-based anionic surfactant, such as in Comparative Example 6, and the case where the average secondary particle diameter of the cuprous oxide particles was too large, such as in Comparative Example 7, the antibacterial performance decreased. In the case where the average secondary particle diameter of the cuprous oxide particles was too large, such as in Comparative Example 7, the transparency also decreased.

When the non-volatile matter content in the coating agent composition in Comparative Example 8 was analyzed, it was confirmed that the content of the cuprous oxide particles exceeded 50 parts by mass in 100 parts by mass of the non-volatile matter content in the coating agent composition. As a result, the adhesion performance decreased. In addition, when the non-volatile matter content in the coating agent composition in Comparative Example 9 was analyzed, it was confirmed that the content of the cuprous oxide particles was less than 0.1 part by mass in 100 parts by mass of the non-volatile matter content in the coating agent composition. Thus, the antibacterial performance decreased since the content of the cuprous oxide particles was small.

The entire content of Japanese Patent Application No. P2013-036790 (filed on Feb. 27, 2013) is incorporated herein by reference.

Although the present invention has been described above by reference to the examples, the present invention is not limited to the descriptions thereof, and it will be apparent to those skilled in the art that various modifications and improvements can be made.

INDUSTRIAL APPLICABILITY

The cuprous oxide particle dispersion liquid according to the present invention can be prepared by way of a stirring process so as to facilitate the synthesizing process thereof. Further, the cuprous oxide particle dispersion liquid can keep high dispersibility of the cuprous oxide particles even when the concentration of the cuprous oxide particles increases. Accordingly, the transparency of the coating agent composition containing the cuprous oxide particles and the antibacterial/antiviral member using the coating agent composition can be improved. In addition, the antibacterial/antiviral member has a high antibacterial/antiviral property since the content of the cuprous oxide particles is high.

The invention claimed is:

1. A cuprous oxide particle dispersion liquid, comprising:
   cuprous oxide particles;
   20 to 100 parts by mass of a phosphate ester-based anionic surfactant per 100 parts by mass of the cuprous oxide particles; and
   500 to 10000 parts by mass of an organic solvent per 100 parts by mass of the cuprous oxide particles,
   wherein the cuprous oxide particles have an average primary particle diameter of 2 nm to 80 nm and have an average secondary particle diameter of 50 nm to 150 nm, the average secondary particle diameter being measured by dynamic light scattering using cumulant analysis.

2. A coating agent composition, comprising:
   the cuprous oxide particle dispersion liquid according to claim 1; and
   a binder resin,
   wherein the cuprous oxide particles are contained in a range from 0.1 to 50 parts by mass in 100 parts by mass of a non-volatile matter content of the coating agent composition.

3. An antibacterial/antiviral member, comprising:
   a substrate; and
   a coating film formed on the substrate and containing the coating agent composition according to claim 2.

* * * * *